US006824983B1

(12) United States Patent
Rak et al.

(10) Patent No.: US 6,824,983 B1
(45) Date of Patent: Nov. 30, 2004

(54) METHOD FOR THE MUTAGENESIS OF NUCLEOTIDE SEQUENCES IN PLANTS ALGAE OR FUNGI

(75) Inventors: Bodo Rak, Freiburg (DE); Ralf Reski, Oberried (DE); Susanne Zimmermann, Tübingen (DE); Marie-Christine Guitton, Jungholtz (FR); Elke Duwenig, Ludwigshafen (DE); Annette Freund, Limburgerhof (DE)

(73) Assignees: BASF Plant Science GmbH, Ludwigshafen (DE); Albert-Ludwigs-Universitat Freiburg, Freiburg (DE)

(*) Notice: Subject to any disclaimer, the term of this patent is extended or adjusted under 35 U.S.C. 154(b) by 0 days.

(21) Appl. No.: 10/130,428

(22) PCT Filed: Nov. 16, 2000

(86) PCT No.: PCT/EP00/11326

§ 371 (c)(1),
(2), (4) Date: May 17, 2002

(87) PCT Pub. No.: WO01/38509

PCT Pub. Date: May 31, 2001

(30) Foreign Application Priority Data

Nov. 26, 1999 (EP) .............................................. 99123611

(51) Int. Cl.[7] .......................... C12Q 1/68; C07H 21/04; C12N 15/70
(52) U.S. Cl. ....................... 435/6; 435/69.1; 435/320.1; 435/410; 435/440; 435/449; 435/471; 536/23.1; 536/23.4; 536/24.3
(58) Field of Search .......................... 435/6, 440, 69.1, 435/449, 471, 410, 320.1; 536/23.1, 23.4, 24.3

(56) References Cited

U.S. PATENT DOCUMENTS 5,767,373 A * 6/1998 Ward et al.
5,783,431 A * 7/1998 Peterson et al.
5,811,238 A * 9/1998 Stemmer et al.

FOREIGN PATENT DOCUMENTS

WO  WO92/01047  * 1/1992

OTHER PUBLICATIONS

Reski, "Physcomitrella and Arabidopsis; the David and Goliath of reverse genetics", Trends in Plant Science, vol. 3, No. 6, Jun. 1998, pp. 209–210.
Strepp et al, "Plant nuclear gene knockout reveals a role in plastid division for the homolog of the bacterial cell division protein FtsZ, an ancestral tubulin", Proceedings of the National Academy of Sciences of the USA, vol. 95, Apr. 1998, pp. 4368–4373.
Reski, "Molecular genetics of Physcomitrella", PLANTA, vol. 208, No. 3, May 1999, pp. 301–309.

Schaefer et al., "Efficient gene targeting in Physcomitrella patens" Plant Journal, vol. 11, No. 6, Jun. 1997.
Mengiste et al, "Prospects for the Precise Engineering of Plant Genomes by Homologous Recombination", Biological Chemistry, vol. 380, No. 7–8, Jul. 1999–Aug. 1999, pp. 749–758.
Fotheringham et al Molecular and Cellular Biology Sep. 1989, vol. 9, No. 9, pp. 4052–4055 "Cloning and Disruption of Ustilago maydis Genes".
Sanger et al Proc.Natl. Acad. Sci. USA vol. 74, No. 12, pp. 5463–5467 Dec. 1977 "Biochemistry DNA sequencing with chain–terminating inhibitors".
Engel Amer. J. Bot. 55(4):pp. 438–446,. 1968 "The Induction of Biochemical and Morphological Mutants in the Moss Physcomitrella Patens".
Rother et al J. Plant Physiol. vol. 143, pp. 72–77 (1994) "Fate of a Mutant Macrochloroplast in Somatic Hybrids".
Schreil J. of Cell Biol. vol. 22, 1964, pp. 1–20 "Studies on the Fixation of Artificial and Bacterial DNA Plasms for the Electron Microscopy of Thin Sections".
J. Ultrastructure Research 26, 31–43 (1969) pp. 31–43.
Spurr, J. Ultrastructure Research 26, 31–43 (1969) "A Low Viscosity Epoxy Resin Embedding Medium for Electron Microscopy".
Schnetz et al J. of Bacteriology, vol. 169, No. 6, Jun. 1987, pp. 2579–2590 "β–Glucoside (bgl) Operon of *Escherichia coli* K–12: Nucleotide Sequence, Genetic Organization, and Possible Evolutionary Relationship to Regulatory Components of Two *Bacillus subtilis* Genes".
Reynolds, Dept. of Anatomy, Harvard Medical School, Brief Notes 1963, Cell Biol, 17 pp. 208–221 "The Use of Lead Citrate at High pH as an Electron–Opaque Stain in Electron Microscopy".
Schaefer et al Mol. Gen. Genet. (1991) 226: 418–424 "Stable transformation of the moss *Physcomitrella patens*".
Timberlake et al Science vol. 244, Jun. 1989 pp. 1313–1317 "Genetic Engineering of Filamentous Fungi".
Kempin et al Nature vol. 389, Oct. 1997 pp. 802–803 "Targeted disruption in *Arabidopsis*".
De Lozanne et al Science, May 29, 1987vol. 236, pp. 1086–1091 "Disruption of the *Dictyostelium* Myosin Heavy Chain Gene by Homologous Recombination".

(List continued on next page.)

*Primary Examiner*—BJ Forman
(74) *Attorney, Agent, or Firm*—Morrison & Foerster LLP

(57) ABSTRACT

The invention relates to a method for the mutagenesis of eucaryotic nucleotide sequences, preferably from plants, algae and/or fungi and a method for the production of genetically modified eucaryotic cells. The subject of the invention is the genetically altered nucleotide sequences of the type disclosed, vectors containing such nucleotide sequences, as well as genetically altered eucaryotic cells, tissue and/or parts of plants, algea and/or fungi and/or regenerated whole plants and the use thereof.

16 Claims, 4 Drawing Sheets

OTHER PUBLICATIONS

Figure 1:
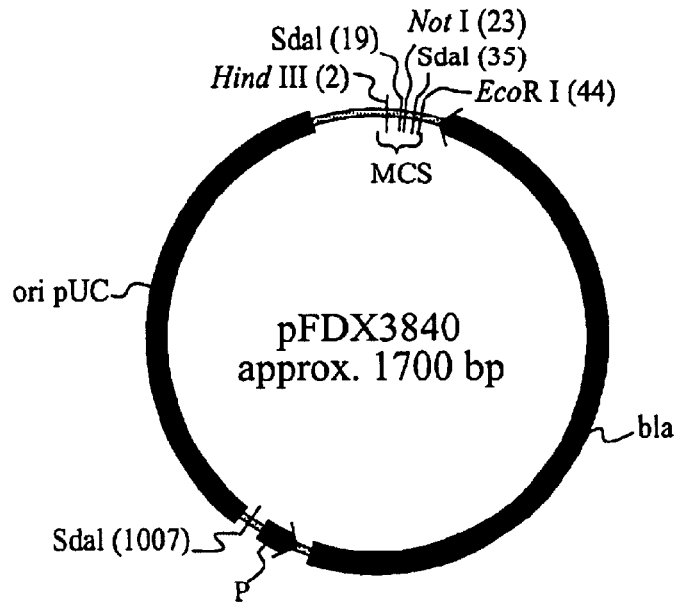

Datta et al J. of Gen. Microbiology (1972), 72, 349–355 "Trimethoprim Resistance Conferred by W Plasmids in Enterobacteriaceae".

Thykjaer et al Plant Molecular Biology 35:523–530, 1997 "Gene targeting approaches using positive–negative selection and large flanking regions".

Avila et al Plasmid 20, 155–157 (1988) "Short Communications Physical and Genetic Map of the IncW plasmid R388".

Reski et al Planta (1985) 165:354–358 "Induction of budding on Chloronemata and caulonemeta of the moss, *Physcomitrella patens* using isopentenyladenine".

Grimm et al Mol. Gen. Genet. (1988) 215:87–93 "Observations on integrative transformation in *Schizosaccharomyces pombe*".

Struhl Nature vol. 305 Sep. 1983 pp. 391–397 "The new yeast genetics".

* cited by examiner

SEQUENCE LISTING

```
<160> NUMBER OF SEQ ID NOS: 10

<210> SEQ ID NO 1
<211> LENGTH: 85
<212> TYPE: DNA
<213> ORGANISM: Artificial Sequence
<220> FEATURE:
<223> OTHER INFORMATION: Description of Artificial Sequence:primer IRL

<400> SEQUENCE: 1
cctagggccg cttaaggtgc acgcgcacgc gtgcatgcaa cgtacgtttt cgttccattg      60
gccctcaaac cccgtcgacg atatc                                           85

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence:primer IRR

<400> SEQUENCE: 2
agagcgcgat atcggggttt gagggccaat ggaacgaaaa cgtacgttct g              51

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:oligo 1

<400> SEQUENCE: 3
ctgcagcgtc cgaaatatta taaattatcg c                                    31

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: oligo 2

<400> SEQUENCE: 4
cgatatttga tttaggatac acctagg                                         27

<210> SEQ ID NO 5
<211> LENGTH: 21
<212> TYPE: DNA
<213> ORGANISM: Artificial Sequence
```

```
-continued

<220> FEATURE:
<223> OTHER INFORMATION: Description of Artificial Sequence: primer PT1

<400> SEQUENCE: 5
gaggctattc ggctatgact g                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer PT2

<400> SEQUENCE: 6
atcgggagcg gcgataccgt a                                             21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer Ppf4

<400> SEQUENCE: 7
ggagctgaca tggttttcgt                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer RT1

<400> SEQUENCE: 8
tgtcgtgctc caccatgttg                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer RT4

<400> SEQUENCE: 9
gttgagcata taagaaaccc                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer Ppf5

<400> SEQUENCE: 10
aacccatact taactaggca                                               20
```

METHOD FOR THE MUTAGENESIS OF NUCLEOTIDE SEQUENCES IN PLANTS ALGAE OR FUNGI

This application is the US national phase of international application PCT/EP00/11326 filed 16 Nov. 2000 which designated the U.S.

The present invention relates to a method for the mutagenesis of eukaryotic nucleotide sequences, preferably from plants, algae and/or fungi, and to a method of generating such genetically modified eukaryotic cells.

A possible method of elucidating gene functions is the inactivation of genes and the subsequent observation of the effects on the metabolism or the phenotype of the modified system.

In particular gene inactivation by insertion mutagenesis has proved difficult in eukaryotic systems. The success of gene inactivation by homologous recombination in the host genome depends essentially on the ratio in which undesired, site-independent recombination occurs over site-specific homologous recombination. This ratio differs widely in eukaryotic organisms. A sufficiently high efficiency of the method for generating a large number of mutants is only described for lower eukaryotic organisms and starting from genomic DNA. Efficacies of above 10% have previously only been demonstrated in yeasts (Grimm & Kohli, 1988, MGG 215, 87–93; Struhl 1983, Nature 305, 391–397), various filamentous fungi (Fotheringham & Holloman, 1989, Mol. Cell Biol. 9, 4052–4055; Kronstad et al., 1989, Gene 79, 97–106; Paietta & Marzluff, 1985, Mol. Cell Biol. 5, 1554–1559; Timberlake & Marshall, 1989, Science 244, 1313–1317) and in Dictyostelium discoideum (De Lozanne & Spudich, 1987, Science 236, 1086–1091).

Homologous recombination in plants has previously been reported from Arabidopsis thaliana (Kempin et al., Nature 1998, 389, 802–803) for the AGL5 gene, an MADS box factor and for the TGA3 locus (Miao & Lam 1995, Plant Journal 7, 359–365). Here, however, only individual events were observed, and these permit no information on the statistic frequency (Puchta 1998, Trends Plant Sci. 3 (3), 77–80). Phenotypic changes were not observed in these cases. In the case of the AGL5 gene, one of 750 analyzed plants had a site-specific mutation (which corresponds to a recombination rate of 0.13%); in the case of the TGA3 locus, one event was found out of 2580 mutants (which corresponds to a recombination rate of 0.04%). It has been reported for Lotus japonica that no homologous recombination event was identified out of 18974 transformants (Thykjaer et al. 1997, Plant Mol. Biol. 35, 523–530).

Using genomic fragments of single-copy genes, knock-out mutants were obtained in the moss Physcomitrella patens as a consequence of homologous recombination (Schaefer et al., 1997, Plant Journal 11 (6): 1195–1206). The homologous recombination rate was 90%. Again, no change in phenotype was observed in this case.

The utilization of genomic nucleotide sequences for generating mutants is disadvantageous inasfar as the DNA fragments may comprise a variety of operable units or linkages. Operable unit or linkage is understood as meaning the sequential arrangement of individual units and their linkage to each other, such as promoter, coding sequence, terminator and, if appropriate, further regulatory elements in such a way that each of the regulatory elements can fulfill its intended function upon expression of the coding sequence. Site-unspecific insertion may have such a random modifying effect on, for example, promoters that a regulator with novel characteristics arises.

The analysis of the mutants may reveal further problems. If, for example, two genes are disrupted by a nucleic acid fragment, no definite conclusion regarding the involvement of a gene can subsequently be drawn since the contribution of an individual gene to the effect to be observed cannot be assessed. This would first have to be tested by more complicated analyses, such as, for example, sequencing of the genomic fragments used, and by determining the type of insertion in the plant and its effect on the genomic arrangement of modified gene segments.

The inactivation of genes by the insertion mutagenesis of genomic DNA by means of homologous recombination by known methods furthermore has a further considerable disadvantage. Thus, for example, the analysis of the entire genome of a host system requires the complicated construction of several thousand individual constructs of genomic origin, which constructs must also be retransformed individually into the host cell, before analysis of the mutants obtained by homologous recombination is made possible. Such genomic mutation approaches are thus not very economical and unsuitable for a routine throughput of experimental set-ups of substantial size, for example with the aim of obtaining a "saturated" mutagenesis of the entire host genome.

It is an object of the present invention to provide a simple and efficient method for the mutagenesis in eukaryotic cells which no longer has the abovementioned disadvantages.

We have found that this object is achieved by a method for the mutagenesis of eukaryotic nucleotide sequences in which a genomic nucleotide sequence and/or cDNA sequence from eukaryotic organisms is transferred into a microorganism, the eukaryotic nucleotide sequence is genetically modified in the microorganism by sequence-independent insertion mutagenesis, and this genetically modified eukaryotic nucleotide sequence is subsequently isolated from the microorganism. Only one transposition event takes place per transferred eukaryotic nucleotide sequence. The transfer of eukaryotic cDNA is preferred.

In a further variant of the method according to the invention, the sequence-independent insertion mutagenesis is achieved by cointegrate formation during the conjugation between two microorganisms. Here, the eukaryotic nucleotide sequence is transferred into a microorganism which then acts as donor cell; the eukaryotic nucleotide sequence is subsequently mutated in the microorganism by sequence-independent insertion mutagenesis, during which process a cointegrate is first formed, the cointegrate formed is then transferred into another microorganism (receptor) via conjugation, the cointegrate is broken down in the receptor, during which process the eukaryotic nucleotide sequence is genetically modified by insertion of a heterologous nucleotide sequence, and this genetically modified eukaryotic nucleotide sequence is isolated from the microorganism. Heterologous DNA is to be understood in accordance with the invention as meaning DNA which does not naturally occur in eukaryotic organisms, i.e. which originates from prokaryotic organisms or, if appropriate, from viruses or phages, and which is replicated in microorganisms. In a preferred variant of the method according to the invention, cDNA sequences from eukaryotic organisms, preferably from plants, algae and/or fungi, are employed.

It is essential for the present method that the mutagenesis in the microorganism takes place with a high degree of efficiency, preferably with a relative frequency post-selection in a range of from approximately 90 to 100%, especially preferably of more than 90 to 99%, in particular 99.9%. In accordance with the invention, only one insertion event takes place per nucleotide sequence.

Since, in accordance with the invention, the mutagenesis of the eukaryotic nucleotide sequence takes place in a sequence-independent manner, that is to say randomly, by insertion of a heterologous nucleotide sequence, the method according to the invention is advantageously distinguished by the fact that the eukaryotic nucleotide sequence can be mutated without it being necessary to know its exact nucleotide sequence or specific restriction cleavage sites. Based on a selected region of a eukaryotic nucleotide sequence, a multiplicity of different (chimeric) eukaryotic nucleotide sequences, which merely differ from each other by the insertion site of the heterologous nucleotide sequence in the eukaryotic DNA, are generated in accordance with the invention by the sequence-independent mutagenesis.

Furthermore, the method according to the invention is also suitable for the mutagenesis of a very large number of different eukaryotic nucleotide sequences as are present for example in the form of a eukaryotic genetic library. A considerable advantage of the method according to the invention is that for example a complete genetic library can be genetically modified in a single mutagenesis set-up. In this context, a eukaryotic genetic library of genomic nucleotide sequences or else starting from cDNA may be used, the use of cDNA being preferred. In principle, both the use of natural eukaryotic nucleotide sequences and the use of chemically synthesized nucleotide sequences are possible. Chemical synthesis in this context can be effected starting from transcription products, as a rule total RNA or poly-(A)$^+$ RNA, or else for example making use of protein sequences taking into consideration the codon usage of the eukaryotic cells.

In accordance with the invention, the eukaryotic genetic library is mutagenized homogeneously in a single mutagenesis set-up with a statistic probability in the range of from 90–100%, preferably 90–99%, especially preferably 99.9%.

Since the principle of the method according to the invention is based on sequence-independent mutagenesis, the origin of the eukaryotic DNA is of minor importance. The eukaryotic DNA employed may take the form of nucleotide sequences from plants, algae and/or fungi. In accordance with the invention, a nucleotide sequence from lower or higher plants is employed. A nucleotide sequence from lower plants of the genus Physcomitrella, Funaria, Ceratodon or Dicranum is preferably employed. A nucleotide sequence from Physcomitrella patens is especially preferably employed. The fungi can take the form of yeasts and/or filamentous fungi, preferably phytopathogenic fungi, especially preferably of the genus Fusarium. Other eukaryotic systems and DNA isolated therefrom are also feasible. The present invention is not limited by the above information on the origin of the DNA to be mutagenized.

Figure 2:
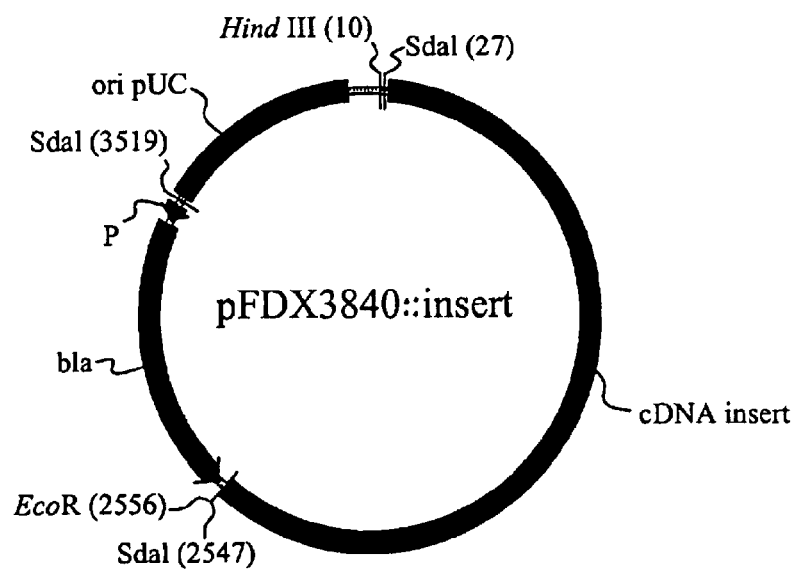
Figure 5:
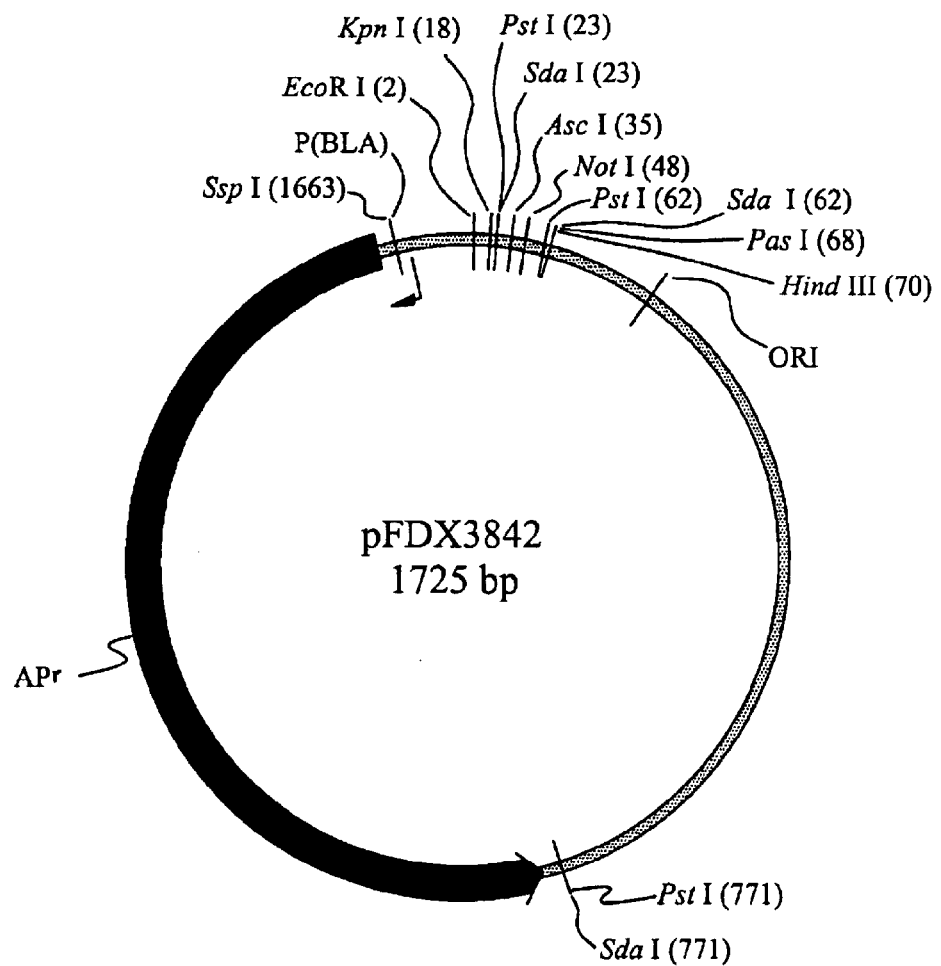
Figure 6:
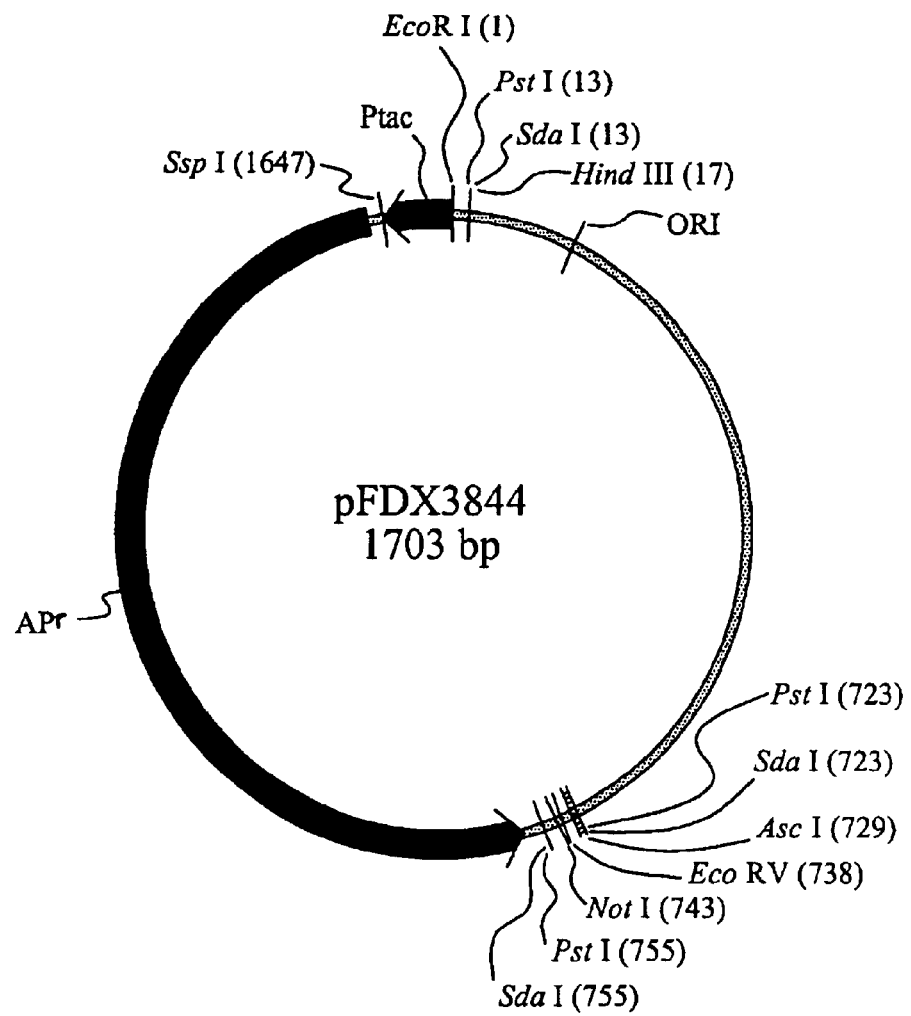

In accordance with the invention, the eukaryotic nucleotide sequence is transferred into a suitable microorganism by methods known per se. To this end, the eukaryotic nucleotide sequence used can be introduced into a suitable vector, for example as shown in FIG. 1. A preferred vector is one which comprises natural nucleotide sequences isolated from eukaryotic cells and/or nucleotides synthesized chemically making use of eukaryotic DNA or in accorance with the codon usage of the eukaryotic cell. In further embodiments of the present invention, a vector comprising a eukaryotic nucleotide sequence and additional functional nucleotide sequences, for example as shown in FIG. 2, is transferred into a microorganism. Additional functional nucleotide sequences are understood as meaning in accordance with the invention for example a replication origin for multiplication in bacteria, a selection marker, recognition sites for restriction endonucleases suitable for cloning the eukaryotic DNA, and others. The vectors shown in FIG. 1, 2, 5 or 6 comprise examples of such constructs. The invention therefore also relates to vectors for use in a method of the abovementioned type with characteristics shown in FIG. 1, 2, 5 or 6. The vectors shown in FIG. 5 or 6 are derivatives of the vector shown in FIG. 1.

Figure 3:
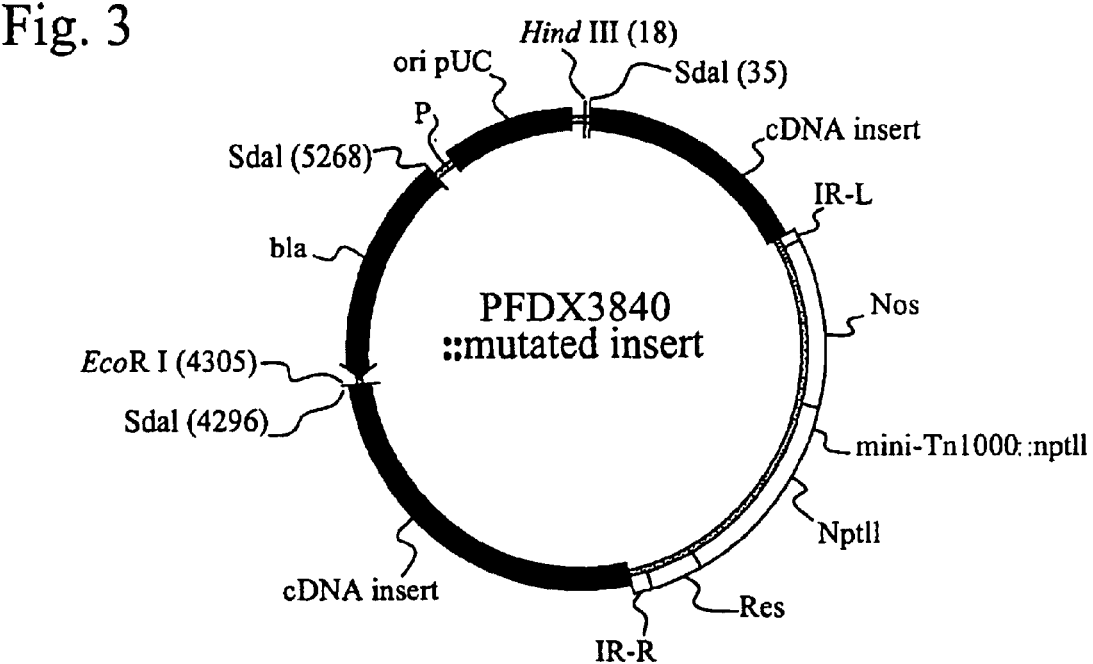

The present invention also relates to the genetically modified eukaryotic DNA resulting from the method according to the invention and/or to a population of resulting genetically modified DNA sequences. The invention furthermore relates to a vector comprising genetically modified eukaryotic DNA generated by the present method. A vector with characteristics are shown in FIG. 3 is preferred. In addition, the present invention also relates to a genetically modified microorganism comprising a genetically modified eukaryotic DNA of the above-described type or a vector comprising such a genetically modified eukaryotic DNA.

It is essential for the method according to the invention that the mutagenesis of the eukaryotic nucleotide sequence in a microorganism is effected by inserting a heterologous nucleotide sequence, preferably of prokaryotic origin. In accordance with the invention, the inserted prokaryotic nucleotide sequence especially preferably takes the form of a nucleotide sequence which has characteristics for transposition. In one embodiment of the present invention, a mini-transposon is used, which, in accordance with the invention, is reduced to the essential features required for transposition. In particular, it takes the form of what is known as the mino-transposon mini-Tn1000::nptll.

It is a further advantage of the method according to the invention that the prokaryotic nucleotide sequence used for insertion into the eukaryotic nucleotide sequence is only capable of transposition in prokaryotic organisms, but not in eukaryotic organisms. Accordingly, the mutations generated by the method according to the invention in the eukaryotic nucleotide sequence is distinguished by the fact that it is essentially stable.

Microorganisms which are employed in accordance with the invention in the above-described method are those which have the necessary characteristics for transposition and conjugation. The microorganism used in accordance with the invention comprises a transposase gene and/or a resolvase gene in replicable form. Preferably, the microorganism employed in accordance with the invention is distinguished by the fact that the transposase gene and/or the resolvase gene is under the control of an inducible promoter. Preferred in this context are, for example, IPTG-inducible promoters, arabinose-inducible promoters such as, for example, the araBAD promoter, or temperature-inducible promoters such as, for example, the phage λ promoters PL or PR, which, in turn, are controlled by the thermosensitive repressor c1857. The genes required for transposition and conjugation may also be present in the microorganism in transient form, i.e. initially in cryptic form, and activated only under specific circumstances.

Figure 4:
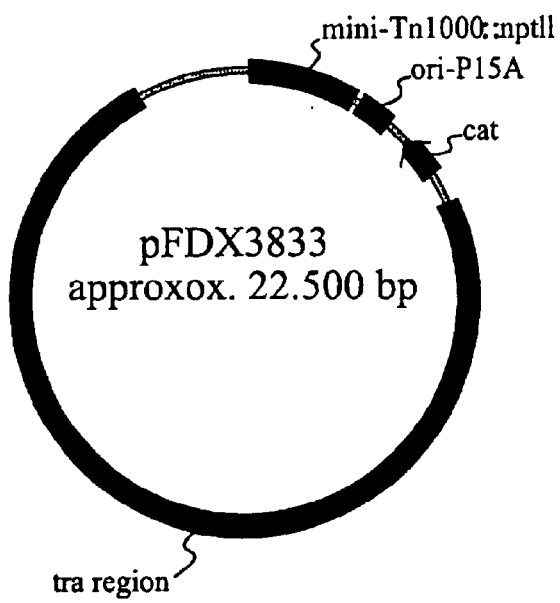

The characteristics regarding transposition and conjugation which have been illustrated above can be encoded chromosomally and/or conferred by vectors in the microorganism used in accordance with the invention. In accordance with the invention, the genetically modified microorganism comprises, in particular, a vector as shown in FIG. 4. This vector confers the necessary characteristics for conjugation between a donor cell and a receptor cell and for the transfer of nucleotide sequences. Moreover, this vector comprises a prokaryotic nucleotide sequence which is suitable for transposition. Preferably, the microorganism employed in the method according to the invention is a bacterium of the genus Enterobacteriaceae or Bacillaceae. The bacterium *Escherichia coli* is especially preferably used, in particular the non-pathogenic cell line *E. coli*K12.

The present invention furthermore relates to a method of generating genetically modified eukaryotic cells of plants, algae and/or fungi or their progeny, a genetically modified eukaryotic nucleotide sequence (which has previously been generated in accordance with the method according to the invention) being transferred into one of these abovementioned eukaryotic host cells, the transformed eukaryotic host cell is incubated under conditions which make possible and/or which trigger a targeted homologous recombination of the introduced genetically modified eukaryotic nucleotide sequence into the genome of the host cell, the eukaryotic host cells which comprise integrated into their genome a genetically modified eukaryotic nucleotide sequence of the abovementioned type are subsequently identified, and corresponding tissue of plants, algae and/or fungi and/or intact plants are regenerated from these cells.

The "conditions" which make possible and/or which trigger a targeted homologous recombination in the eukaryotic cell which has been transformed in accordance with the invention are, for the purposes of the invention, for example the incubation of the cells in selection medium or a change in the culture temperature. In one embodiment of the invention, for example, a culture in kanamycin- and/or G418-containing culture medium and/or an increase in the culture temperature of from, for example, 37° C. to 42° C., can make possible and/or can trigger the insertion mutagenesis according to the invention of a eukaryotic DNA.

In addition, the homologous recombination in this method according to the invention takes place at a high degree of efficiency, which, however, depends on the length of the eukaryotic DNA fragment inserted. Preferably, the homologous recombination takes place with a relative frequency post-selection in a range of from approximately 0.1 to 99.9%, especially preferably of from 1 to 90%, in particular of more than 10%.

In accordance with the invention, the present method comprises the use of a genetically modified eukaryotic nucleotide sequence or a vector comprising a genetically modified eukaryotic nucleotide sequence which is prepared in the manner described further above, likewise in accordance with the invention.

As already described, the method according to the invention gives rise to a multiplicity of genetically modified, chimeric nucleotide sequences which differ from each other only by the insertion site of the heterologous nucleotide sequence. This multiplicity of genetically modified eukaryotic nucleotide sequences is exploited in accordance with the invention via homologous recombination for the generation of a multiplicity of genetically modified eukaryotic organisms, i.e. plants, algae and/or fungi. That is, the method according to the invention gives rise to a population of eukaryotic cells comprising differently genetically modified nucleotide sequences. In this context, the individual eukaryotic cells are distinguished by the fact that they are mutated within a narrow genetic region, but that they all differ from each other by the exact site of mutation. A further advantage of the method according to the invention is that it gives rise to a population of genetically modified eukaryotic cells whose genome is modified at different sites with a statistic probability in the range of from 90–100%, preferably more than 90–99%, especially preferably 99.9%, and which is thus suitable for establishing a eukaryotic mutant genetic library.

This method according to the invention is furthermore distinguished by the fact that the homologous recombination of the genetically modified eukaryotic nucleotide sequence into the genome of the eukaryotic host cell leads to a phenotypically discernible and/or measurably modified phenotype in the plant. That is, in a particular embodiment of the present invention, a eukaryotic nucleotide sequence can be chosen for use in the method according to the invention in such a way that the insertion mutagenesis is effected in particular within the coding region of an active gene. Owing to the insertion site, the functionality of the mutated gene loci can be modified to a different degree, which permits the detailed mapping of various domains of a gene. In accordance with the invention, the resulting genetically modified eukaryotic nucleotide sequence is destroyed specifically in one gene function, i.e. negative mutants are generated.

The integration site of the heterologous nucleotide sequence is identified in accordance with the invention by recombinant methods. Recombinant methods are understood as meaning, in the present context, all of the methods known per se by means of which the integration of known nucleotide sequences into the corresponding target sequence can be identified. Examples which may be mentioned are the hybridization with specific and suitably labeled probes, the identification of the target site via polymerase chain reaction (PCR), or the use of specific antibodies.

The method according to the invention is furthermore distinguished by the fact that the eukaryotic host cells employed are cells of lower and/or higher plants. Eukaryotic host cells which are preferably employed are cells of the genus Physcomitrella. Cells of Physcomitrella patens are especially preferably employed. Genetically modified algae and/or fungi are also generated in accordance with the invention by the method illustrated hereinabove. Genetically modified filamentous fungi are preferably generated, especially preferably phytopathogenic fungi, and in particular fungi of the genus Fusarium.

A further advantage of the method according to the invention is that the prokaryotic nucleotide sequence, or parts thereof, which is (are) used for insertion into the eukaryotic nucleotide sequence is (are) only capable of transposition in prokaryotic organisms, but not in eukaryotic organisms. Accordingly, the mutation, in the eukaryotic nucleotide sequence, which has been generated by the method according to the invention is distinguished by the fact that it is essentially stable.

The present invention furthermore relates to a genetically modified eukaryotic cell of plants, algae and/or fungi or its progeny generated by the abovementioned methods. Also encompassed are genetically modified eukaryotic cell tissue, reproductive material, seeds and/or spores of genetically modified eukaryotic cells of plants, algae and/or fungi. Also encompassed in accordance with the invention are intact plants and/or plant parts comprising genetically modified eukaryotic cells of the above-described type and/or capable of regeneration from such genetically modified cells. Preferred as genetically modified eukaryotic cell or its progeny is a cell of the genus Physcomitrella. This is especially preferably a cell of Physcomitrella patens.

The genetically modified eukaryotic cell according to the invention or its progeny is furthermore distinguished by the fact that it is modified in a phenotypically discernible form and/or has a positively measurably modified phenotype. In accordance with the invention, the genetically modified eukaryotic cell and its progeny bears the integrated heterologous (prokaryotic) nucleotide sequence predominantly in coding sequence regions. This is why the functionality of the genes concerned and of the gene products derived therefrom in the eukaryotic cells and their progeny which have been genetically modified in accordance with the invention is modified to a different degree as a function of the insertion site of the prokaryotic nucleotide sequence. In a particular embodiment of the present invention, the genes concerned, of the genetically modified eukaryotic cells and their progeny, no longer have any functionality. These mutations are also termed negative mutations or what is known as knock-out or loss-of-function mutations. The corresponding genetically modified eukaryotic cells and. their progeny are analogously termed negative mutants or knock-out mutants.

The genetically modified eukaryotic cells according to the invention are furthermore distinguished by the fact that they comprise genetically stably modified nucleotide sequences owing to sequence-independent (random) insertion of a heterologous nucleotide sequence. Preferably, the eukaryotic cell which has been genetically modified in accordance with the invention and its progeny comprise a stably inserted nucleotide sequence of prokaryotic origin. In this context, the genetically modified eukaryotic cells according to the invention and their progeny are distinguished by the fact that they comprise a nucleotide sequence which can be transposed into prokaryotic organisms and not into eukaryotic organisms, or parts of such a nucleotide sequence.

The present invention furthermore relates to the use of a vector as shown in FIG. 1, FIG. 5, FIG. 6 for cloning, and the subsequent mutagenesis of a eukaryotic nucleotide sequence. Also encompassed in accordance with the invention are the resulting vectors comprising a eukaryotic nucleotide sequence provided for mutation (hereinbelow termed derivatives of the vectors as shown in FIG. 5 or FIG. 6). The invention furthermore relates to the use of the vector as shown in FIG. 2 or derivatives of the vectors as shown in FIG. 5 or FIG. 6 for generating a genetically modified eukaryotic nucleotide sequence by above-described methods. The invention further relates to the use of the above-mentioned vectors, preferably of the vectors as shown in FIG. 2, derivatives of FIG. 5 or FIG. 6 and a vector as shown in FIG. 4 for use in a microorganism for the mutagenesis of eukaryotic nucleotide sequences.

The genetically modified eukaryotic cells are furthermore employed for identifying functional nucleotide sequences in eukaryotic cells and/or for the characterization of eukaryotic nucleotide sequences of unknown function (functional genome analysis).

Moreover, the present invention relates to the use of genetically modified eukaryotic cells for use in fields of agriculture, pharmacy and/or medicine.

In the following text, the present invention is illustrated in greater detail by examples which, however, do not limit the invention:

1) General Cloning Methods:

Cloning methods such as, for example, restriction cleavages, agarose gel electrophoresis, purification of DNA fragments, transfer of nucleic acids to nitrocellulose and nylon membranes, linking DNA fragments, transformation of *Escherichia coli* cells, growing bacteria and the sequence analysis of recombinant DNA were carried out as described by Sambrook et al. (1989) (Cold Spring Harbor Laboratory Press: ISBN 0-87969-309-6).

2) Chemicals:

Unless otherwise specified in the text, the chemicals used were obtained in analytical-grade quality from Fluka (Neu-Ulm), Merck (Darmstadt), Roth (Karlsruhe), Serva (Heidelberg) and Sigma (Deisenhofen). Solutions were made up with purified, pyrogen-free water, hereinbelow termed $H_2O$, from a Milli-Q Water System water purification system (Millipore, Eschborn). Restriction endonucleases, DNA-modifying enzymes and molecular-biological kits were obtained from AGS (Heidelberg), Amersham (Brunswick), Biometra (Gottingen), Boehringer (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg) Qiagen (Hilden) and Stratagene (Heidelberg). Unless otherwise specified, they were used following the manufacturers' instructions.

3) Plant Material:

In one embodiment of the present invention, plants of the species Physcomitrella patens (Hedw.) B.S.G. from the collection of the University of Hamburg's working group genetics were used. They are based on strain 16/14, which had been collected by H. L. K. Whitehouse in Gransden Wood, Huntingdonshire (England), which had been subcultured by Engel (1968, Am. J. Bot. 55, 438–446) starting with one spore. The plants were propagated via spores and via regeneration of the gametophytes. The haploid spore gives rise to the protonema in the form of chloroplast-rich chloronema and chloroplast-depleted caulonema, which buds after approximately 12 days. These buds grow into gametophores bearing antheridia and archegonia. Fertilization gives rise to the diploid sporophyte with a short seta and the sporogonium, in which the meiospores attain maturity.

4) Plant Culture Conditions:

Plants were grown in a controlled-environment cabinet at an air temperature of 25° C., a light intensity of 55 $\mu$mol $s^{-1}m^{-2}$ (white light; Philips TL 65W/25 fluorescent tubes) and a photo period of 16/8 hours. The moss was grown either in liquid culture using Knop medium modified as described by Reski and Abel (1985, Planta 165, 354–358) or on solid Knop medium with 1% Oxoid agar (Unipath, Basingstoke, England).

The protonemata used for isolating RNA and DNA were grown in aerated liquid cultures. Every 9 days, the protonemata were comminuted and transferred into fresh culture medium.

5) Plasmids:

5.1) pFDX3840, pFDX3842 and pFDX3844 Plasmid pFDX3840 is a minimalized vector for establishing eukaryotic genetic libraries which comprises as few nonessential target sequences as possible for the integration of the mini-transposon outside the eukaryotic DNA insert (FIG. 1). Starting from the commercially available plasmid pUC12, whose sequence is known, the bla gene, which confers ampicillin resistance, and the origin of replication (ori) were amplified via PCR by methods known per se and linked with a multiple cloning site with single restriction cleavage sites (multiple cloning site, mcs). This multiple cloning site comprises, inter alia, cleavage sites for the restriction enzymes in the sequence KpnI, PstI, SdaI, NotI, SdaI and EcoRI. The restriction enzyme SdaI recognizes the octamer 5'CCTGCAGG3', which, as a rule, rarely cuts within naturally occurring nucleotide sequences (rare cutter). Plasmids pFDX3842 and pFDX3844 are derivatives of plasmid pFDX3840. The two last-mentioned plasmids are optimized further with regard to their multiple cloning site, inter alia, i.e. they have fewer single recognition sites for restriction endonucleases.

5.2.) pFDX3840::insert

This is a pFDX3840 derivative in which a eukaryotic DNA insert has been cloned into the NotI cleavage site (FIG. 2). The plasmid pFDX3840 is digested with NotI by customary methods, isolated and ligated to DNA fragments of eukaryotic origin which have suitably compatible ends (prepared by restriction digestion). Owing to the above-described SdaI rare cutter within the multiple cloning site, which flank the eukaryotic DNA inserts, the eukaryotic DNA inserts, which are mutated by insertion mutagenesis as described hereinbelow, can be excised intact from the vector by means of SdaI restriction digestion. The advantage of isolating SdaI restriction fragments of eukaryotic origin is that it gives rise to 4 bp 3' overhangs, which have a positive effect on the efficiency of the recombination events in the subsequent homologous recombination into eukaryotic systems. Eukaryotic DNA can analogously also be cloned using plasmids pFDX3842 or pFDX3844.

5.3.) pFDX3840:: Mutated Insert:

This is the plasmid described under 5.2.) in which the eukaryotic DNA has been mutated by trasposon mutagenesis and insertion of the mini-transposon mini-Tn1000::nptII, as described hereinbelow (FIG. 3).

5.4.) pFDX3832:

Starting from conjugative plasmid R388 (Datta and Hedges, 1972, J. Gen. Microbiol., 72:349–355; Avila and de la Cruz, 1988, Plasmid, 20:155–157; EMBL Accession No: X81123), which is 33 kb in size and bears a conjugative transfer region (tra), an origin of replication of vegetative replication (ori), sulfonamide resistance (Sm) and a trimethoprim resistance (Tp), the portions which are important for conjugation are subcloned and large regions of the vector which are unimportant for the function of the plasmid, in particular resistance genes Sm and Tp, are discarded. The truncated plasmid, which bears the complete functions for conjugation, but no longer bears any resistance genes, was then provided with a chloramphenicol resistance gene (EcoRV-SalI fragment from plasmid pFDX900) and a replication origin for vegetative replication (ori P15A).

Specifically, the vector portion which is essential for conjugation was isolated from plasmid R388 as a 19.5 kb SalI/MscI fragment by restriction digestion and subsequent gel electrophoresis. A 1947 bp BspI-Klenow-SalI fragment was subsequently isolated analogously from plasmid pFDX900 (Rak, B., 1988, University of Freiburg; unpublished), which fragment encodes a chloramphenicol resistance (cat) and bears the vegetative origin of replication p15A. Plasmid pFDX900 itself is a pFDX733 derivative, which bears a chloramphenical resistance (cat) instead of a kanamycin resistance (neo). To this end, a 6994 bp StuI-BamHI Klenow fragment of pFDX733 (Schnetz, et al., 1987, J. Bacteriol., 169:2579–2590) was ligated to a 964 bp Eco0109-TthIII Klenow fragment from pBR325.

Ligation of the 19.5 kb SalI/MscI fragment (tra) from R388 to the 1947 bp BspI Klenow-SalI fragment from plasmid pFDX900 (cat, ori), subsequent transformation into an *E. coli* strain and selection for chloramphenicol resistant transformants by methods known per se gave rise to plasmid pFDX3832.

5.5) pFDX3809

Plasmid pFDX3809, which bears a 1753 bp EcoRV fragment of the mini-transposon (mini-Tn1000::nptII), is obtained by the cloning steps described hereinbelow: The left inverted repeat (IRL) was cloned into the EcoRV cleavage site of the commercially available pBluescript KS2 in the form of a synthetic oligonucleotide (resulting plasmid pFDX3803). Then, the right inverted repeat (IRR) was cloned between the PstI and the XbaI cleavage site of pFDX3803 (resulting plasmid pFDX3804). The resolution site (res) was amplified with the oligonucleotides shown hereinbelow (oligo 1, oligo 2) starting from plasmid pFDX291 (pACYC177 derivative, into which Tn1000 integrated during a conjugation starting from an F plasmid; Rak, B., University of Freiburg; unpublished) and cloned into the EcoRV cleavage site of the commercially available vector pBluescript KS2 (resulting plasmid pFDX3806). Then, plasmid pFDX3804 and plasmid pFDX3806 were digested separately with the restriction enzymes HindIII/PstI and ligated with the resulting plasmid pFDX3807. For insertion of a multiple cloning site with single restriction cleavage sites (mcs; multiple cloning site), plasmid pFDX3803 was digested in a restriction digest with AvrI and XbaI. A corresponding AvrI/XbaI fragment was isolated from plasmid pFDX3807 and ligated with the above-described pFDX3803 restriction digest to give plasmid pFDX3808, which now bears a mini-transposon. Then, an nptII gene cassette under the control of the nos promoter was additionally introduced into this mini-transposon. This nptII gene cassette comprises the nos promoter upstream of the nptII gene and the 3'-untranslated region of the nos terminator downstream of the nptII gene. This gene cassette was isolated from plasmid pBSNNN (Reski, R., University of Freiburg) by HindIII/BamHI Klenow restriction digestion starting from the bacterial transposon Tn5, the origin of the nptII gene being the bacterial transposon Tn5. This fragment was subsequently ligated to plasmid pFDX3808, which had been linearized by MluI Klenow treatment. The resulting construct is termed pFDX3809.

Primers used:

IRL: (SEQ ID NO:1) 5'CCTAGGGCCGCTTAAGGTG-CACGCGCACGCGTGCATGCAACGTAC GTTTTCGTTCCATTGGCCCTCAAAC-CCCGTCGACGATATC3'

IRR: (SEQ ID NO:2) 5'AGAGCGCGATATCGGGGTTTGAGGGC-CAATGGAACGAAAACGTAC GTTCTG3'

Oligo1: (SEQ ID NO:3) 5'CTGCAGCGTCCGAAATAT-TATAAATTATCGC3'

Oligo2: (SEQ ID NO:4) 5'CGATATTTGATTTAGGATA-CACCTAGG3'

5.6.) pFDX3833:

Plasmid pFDX3833 is a pFDX3832 derivative and additionally bears a 1753 bp EcoRV insert from plasmid pFDX3809 (Rak, B., University of Freiburg; unpublished), which contains a mini-transposon (mini-Tn1000::nptII). Mini-Tn1000 consists of functional units IRL-NOS promoter/nptII/NOS terminator-RS-IRR, where the abbreviations have the following meanings: Tn=transposon, IRL/IRR=inverted repeat left/right, nos=*Agrobacterium tumefaciens* nopalin synthase promoter, nptII=neomycin/kanamycin phosphotransferase gene and RS=resolution site. A schematic representation is shown in FIG. 4.

6) Verification of the Functionality of the Conjugative Plasmid pFDX3832:

The conjugation as proof of functionality of the conjugative plasmid was carried out with the aid of the donor strain *E. coli* K12-R2117 (recA⁻ derivative of the *E. coli* wild type K12-W3110). Since the donor strain bears plasmid pFDX3832, it grows in a medium with a concentration of 10 µg/ml chloramphenicol (Cm). The receptor *E. coli* R1037 has a chromosomal streptomycin resistance gene (Strep) and grows in a medium with a streptomycin concentration of 100 µg/ml.

20 ml portions of LB medium (supplemented with the relevant antibiotic) are inoculated with an overnight culture of donor and receptor ($OD_{600}$ start: 0.1). After an $OD_{600}$ of 0.4–0.5 has been reached, 3 ml of the bacterial culture of each donor and receptor are mixed and grown on without selection pressure to an $OD_{600}$ of 0.8. Then, 0.3 ml of the mixture is plated onto medium without selection pressure and the cultures are incubated for 1.5 hours at 37° C. During this period, conjugation takes place, i.e. plasmid pFDX3832 is transferred into the receptor strain. The cells are subsequently washed off and plated in suitable dilutions onto selective medium supplemented with the antibiotics streptomycin (to determine the receptor titer) and streptomycin plus chloramphenicol (to determine the exconjugant titer). The donor cells, which contain plasmid pFDX3832, are only resistant to chloramphenicol, and the receptor cells only to streptomycin. Only receptor cells which have received plasmid pFDX3832 via conjugation are resistant to both antibiotics (Cm and Strep). The conjugation rate is calculated from the number of exconjugants divided by the number of all receptor cells post-conjugation. The conjugation rate for pFDX3832 is 57–86% compared with a conjugation rate of 30–40% which is normally usual for the above-described conditions.

7) Generation of Novel Donor and Receptor Strains of *E. coli*:

Two auxiliary systems are required for the integration of any DNA fragments into the genome of *E. coli* by site-specific recombination at the integration site attB: a) a temperature-sensitive helper plasmid, and b) a vector with λattP sequences and the resolvase or transposase gene, respectively, downstream of an inducible promoter.

a) Temperature-sensitive helper plasmid pFDX3401

The plasmid bears the following characteristics:
ori=origin of replication for vegetative replication
cat=chloramphenical resistance gene
$\lambda cI_{857}^{ts}$=a temperature-sensitive repressor
$\lambda P_R$, a promoter under the control of the repressor
int=integrase gene
$rep^{ts}$=temperature-sensitive vegetative DNA replication b) Cloning vector with polylinker and λattP sequences pFDX3801

The vector bears the following characteristics:
ori=replication origin for vegetative replication
kan=kanamycin resistance gene
The following are present, flanked by two NotI cleavage sites:
λattP=integration site
$Tet^R$=tetracyclin resistance gene
MCS=multiple cloning site with i) or ii) insert
i) $lacI^q$-lacOi-Ptac-lacO1-SD with tnpR=IPTG-inducible promoter with resolvase gene or
ii) $lacI^q$-lacOi-Ptac-lacO1-SD with tnpA=IPTG-inducible promoter with transposase gene The constructs are cloned using three different Shine-Dalgarno sequences (SD) to allow different levels of resolvase and transposase expression, thus finding the optimal enzyme concentrations of resolvase and transposase.

The NotI fragment was isolated from each of the constructs and religated, so that the religated molecules no longer bear an origin of replication and contain the tetracyclin resistance gene for selection.

The three transposase constructs are transformed in each case into the *E. coli* donor strain R2117, which contains the helper plasmid pFDX3401. Each of the three resolvase constructs is transformed into the *E. coli* receptor strain R1037, which likewise contains the helper plasmid pFDX3401.

The bacteria are subsequently plated onto LB medium supplemented with tetracyclin and incubated at a temperature of 42° C.

The temperature-sensitive repressor is thereby inactivated, leading to the synthesis of integrase. The latter catalyzes the site-specific recombination between the λattP site on the NotI fragment and the λattB site in the chromosome, and thus integration of the expression cassette into the chromosome. The rep protein (encoding by the allele $rep^{ts}$), which is essential for the replication of the helper plasmid, is simultaneously inactivated so that replication of the helper plasmid is blocked and the helper plasmid itself is lost during the subsequent bacterial multiplication.

Thus, colonies which are resistant to tetracyclin at 42° C. are selected. They bear the resolvase or transposase constructs integrated into the bacterial chromosome. Starting from overnight cultures, permanent cultures were established in DMSO.

The essential characteristics of the *E. coli* donor and receptor strains are again compiled in the following list:

*E. coli* R2117 derivatives (donor)
conjugative plasmid pFDX3833 with mini-Tn1000::nptII
chromosomally integrated into $\lambda attB:lacI^q-O_i tacOP-tnpA$; $tet^R$
three different Shine-Dalgarno sequences from
a) phage T7 gene 10
b) natural sequence
c) *E. coli* bglG gene
recA⁻
$strep^S$ The abbreviations denote:
$lacI^q$=lactose repressor gene with mutation in the promoter region
tnpA=transposase gene
$O_i tacOP$=tac operator/promoter, the Pribnow box having the consensus sequence TATAAT and the −35 box having the consensus sequence TTGACA. $O_i$ denotes the fact that a second synthetic operator with ideal ($O_i$) binding characteristics for the repressor is present 92 bp upstream (5') of the operator. This leads to cooperative binding of the repressor to the two promoters (loop formation) and thus to a considerably improved repression.

*E. coli* R1037 derivatives (receptor)
conjugative plasmid pFDX3833 with mini-Tn1000::nptII
chromosomally integrated into $\lambda attB:lacI^q-O_i tacOP-tnpR$; $tet^R$
three different Shine-Dalgarno sequences from
d) phage T7 gene 10
e) natural sequence
f) *E. coli* bglG gene
$strep^R$ tnpR denotes resolvase gene.

8) Transformation of the donor strain with eukaryotic DNA:

The *E. coli* donor strain is made competent for DNA transfer by methods known per se. 1 ng–1 µg of eukaryotic DNA or vector DNA (containing ampicillin resistance gene) containing eukaryotic DNA is subsequently employed in the electroporation set-up. When using a DNA library, the amount of DNA is selected on the basis of the skilled worker's experience so that the DNA library in its totality is represented once to twice. The successfully transformed cells are selected on LB medium supplemented by the antibiotics ampicillin (50 µg/ml), chloramphenicol (10 µg/ml) and tetracyclin (10 µg/ml). Starting from suitably grown overnight cultures, permanent cultures were established in DMSO.

9) Conduction:

The donor strain is inoculated into 20 ml of LB medium supplemented with ampicillin (50 µg/ml), chlor-amphenicol (10 µg/ml) and tetracyclin (10 µg/ml) in a 1:100 dilution of the permanent culture in DMSO. The expression of the transposase gene is subsequently induced with IPTG (isopropyl-β-D-thiogalacto-pyranoside).

The *E. coli* receptor strain is inoculated into 20 ml of LB medium supplemented with streptomycin (100 µg/ml) and tetracyclin (6–10 µg/ml) in 1:100 dilution from the permanent culture in DMSO. Again, expression of the resolvase is subsequently induced with IPTG. The two bacterial strains are cultured to an $OD_{600}$ of 0.4. Then, IPTG (final concentration 1 mM) is added, and the bacteria are cultured until an $OD_{600}$ of 0.8 has been reached. 150 µl of each of the donor and the receptor culture are subsequently mixed and plated onto an LB nutrient agar plate without antibiotics, but containing 1 mM IPTG. After the agar plates treated in this way have dried for 10 minutes with the lid slightly ajar, they are incubated for 1.5 hours at 37° C.

After the incubation, the bacteria are washed off with 3 ml of LB medium without antibiotics, plated on selective medium (LB medium supplemented with ampicillin, streptomycin, tetracyclin at concentrations described before) and incubated overnight at 37° C. To act as control and to determine the titer, suitable dilutions are plated onto nutrient agar plates supplemented with streptomycin (to determine the titer of all receptors), streptomycin plus chloramphenicol (to determine the exconjugant titer) and ampicillin plus streptomycin (to determine the exconductant titer). The typical exconjugant rate is 50–80% and the exconductant rate is 6–8%.

The resulting exconductants are washed off from the agar plates. The bacteria which have been washed off are inoculated into 5 liters of selective medium (LB medium supplemented with ampicillin and streptomycin) and grown overnight at 37° C. With this batch, permanent cultures are established in DMSO, and the plasmid DNA is isolated quantitatively from the remaining culture liquid using customary methods, such as, for example, CsCl gradient or affinity chromatography. Then, the DNA obtained is transferred into eukaryotic cells in a suitable manner.

10) PEG-Mediated DNA Transfer:

Physcomitrella patens was transformed using the polyethylene glycol (PEG)-mediated direct DNA transfer into protoplasts. The plasmid DNA to be transformed was purified via Qiagen Tip-500 columns (Diagen, Hilden). The PEG had a molecular weight of 4000 and was always prepared freshly in 3M medium (Schäfer et al., 1991, Mol. Gen. Genet. 226, 418–424: 15 mM MgCl2, 0.1% MES, 0.48 M mannitol, pH 5.6, 580 mosmol) 3 hours before the transformation. All of the solutions used were filter-sterilized.

Protoplasts were isolated by the method of Rother et al. (1994, J. Plant Physiol. 143, 72–77) from liquid cultures. After the last wash step, the protoplasts were taken up in 3M medium, counted, brought to a concentration of $1.2 \times 10^6$ protoplasts/ml with 3M medium and employed immediately for the transformation.

The transformation was carried out by a modification of a method of Schäfer et al. (1991, Mol. Gen. Genet. 226, 418–424) in sterile glass tubes at room temperature. First, 50 µg of plasmid DNA in 100 µl of 0.1 M $Ca(NO_3)_2$ were mixed in the glass tubes with 250 µl of protoplasts, and 350 µl of 40% (w/v) PEG 4000 were subsequently added dropwise with careful swirling. During the subsequent incubation for 30 minutes, the transformation mix was swirled carefully every 5 minutes. It was then diluted stepwise by adding in each case 1, 2, 3 and 4 ml of 3M medium over 20 minutes. The protoplasts were then sedimented for 5 minutes at 70×g, taken up in 3 ml of regeneration medium (Rother et al. 1994, J. Plant Physiol. 143, 72–77) and divided between two petri dishes of 3 cm diameter. The protoplasts were first grown for 24 hours at a low light intensity of 4.9 µmol $s^{-1}$ $m^{-2}$ and subsequently at a light intensity of 46.8 µmol $s^{-1}$ $m^{-2}$ in a controlled-environment cabinet at 25° C. and a 16/8-hour photo period.

The protonemata which had germinated after 5–6 days were transferred to Knop plates covered with sterile cellophane film (Rother et al., 1994, J. Plant Physiol. 143, 72–77). After a further 7 days, the cellophane film, which now contained up to 15-celled protonemata, was transferred to Knop plates with the antibiotic G418 (50 mg/l). To select stable transformants, the surviving protonemata were isolated from the Knop plates on day 26 post-transformation and transferred to Knop plates without cellophane and without antibiotics. After a further 14 days, they were again transferred to selection plates. On day 54 post-transformation, the surviving stably-transformed plants were transferred to liquid culture without antibiotics.

11) Isolation of Total DNA from Physcomitrella Patens:

The data for the isolation of total DNA refer to the work-up of plant material with a fresh weight of one gram.

CTAB buffer: 2% (w/v) N-cetyl-N,N,N-trimethylammonium bromide (CTAB); 100 mM Tris-HCl pH 8.0; 1.4 M NaCl; 20 mM EDTA.

N-Lauroylsarcosine buffer: 10% (w/v) N-lauroyl-sarcosine; 100 mM Tris-HCl pH 8.0; 20 mM EDTA.

The plant material was comminuted with a pestle and mortar under liquid nitrogen to give a fine powder and transferred into 2 ml Eppendorf tubes. The frozen plant material was subsequently covered with 1 ml of disruption buffer (1 ml CTAB buffer, 100 ml N-lauroyl-sarcosine buffer, 20 ml β-mercaptoethanol and 10 ml Proteinase K solution, 10 mg/ml) and incubated for one hour at 60° C. with constant shaking. The resulting homogenate was divided between two Eppendorf tubes (2 ml) and extracted by shaking twice with an identical volume of chloroform/isoamyl alcohol (24:1). For phase separation, the tubes were spun for in each 15 minutes at 8000×g at room temperature. The DNA was subsequently precipitated for 30 minutes with ice-cold isopropanol at −70° C. The precipitated DNA was sedimented for 30 minutes at 4° C. and 10 000 g and resuspended in 180 ml of TE buffer (Sambrook et al., 1989, Cold Spring Harbor Laboratory Press: ISBN 0-87969-309-6). For further purification, the DNA was treated with NaCl (final concentration 1.2 M) and reprecipitated for 30 minutes with twice the volume of absolute ethanol at −70° C. After a wash step with 70% strength ethanol, the DNA was dried and subsequently taken up in 50 ml of $H_2O$ comprising RNAse (final concentration 50 mg/ml). The DNA was dissolved overnight at 4° C., and the subsequent RNAse digestion was carried out for 1 hour at 37° C. The DNA was stored at 4° C.

12) Isolation of Total RNA and Poly-(A)⁺ RNA from Physcomitrella Patens:

Both total RNA and poly-(A)⁺ RNA were isolated in order to study transcripts and to generate cDNA. The total RNA was obtained using the RNeasy Plant Total RNA Kit (Qiagen, Hilden) and the RLT buffer contained therein, in accordance with the manufacturer's instructions. The poly-(A)+ RNA was isolated from the total RNA obtained using the Poly AtractmRNA Isolation System III from Promega (Heidelberg) following the manufacturer's instructions.

After the concentration of the RNA and the poly (A)+ RNA have been determined, the RNA was precipitated by adding 1/10 volume 3 M sodium acetate pH 4.6 and 2 volumes of ethanol and stored at −70° C.

13) Generation of cDNA using Total RNA or Poly-(A)* RNA from Physcomitrella Patens The cDNA was generated using a cDNA synthesis kit from Boehringer Mannheim, Germany, following the manufacturer's instructions. 5 μg of poly-(A)+ RNA from Physcomitrella patens were employed. The cDNA gene library was established in phage λ-GT10 by customary molecular-biological methods as described by Sambrock et al., 1989, Cold Spring Harbor Laboratory Press: ISBN 0-87969-309-6.

14) Northern hybridization:

To carry out the RNA hybridization, 20 mg of total RNA or 1 mg of poly-(A)+ RNA were separated by gel electrophoresis in 1.25% agarose gels containing formaldehyde, as described by Amasino (1986, Anal. Biochem. 152, 304), transferred to positively charged nylon membranes (Hybond N+, Amersham, Brunswick) by capillary transfer using 10×SSC, immobilized by UV light and prehybridized for three hours at 68° C. with hybridization buffer (10% dextran sulfate w/v, 1 M NaCl, 1% SDS, 100 mg herring sperm DNA). The DNA probe was labeled during the prehybridization with alpha-12P DCTP (Amersham, Brunswick) using the 'Rediprime DNA Labelling Kit' (Amersham, Brunswick). The labeled DNA probe was added, and hybridization was effected at 68° C. overnight in the same buffer. The wash steps were carried out twice for 15 minutes with 2×SSC and twice for 30 minutes with 1×SSC, 1% SDS at 68° C. The sealed-in filters were exposed at −70° C. for a duration of 1–14 days.

15) Generation of a Strand-specific DNA Probe for the Hybridization with Tn1000::nptII Sequences:

Probes were generated by methods known per se. They can be radiolabeled or non-radiolabeled, likewise in the customary manner.

16) PCR with Regenerated Plant Material:

PCR was employed for testing the putative plant transformants at an early point in time for bearing transformed DNA. For the test, 0.01–0.05 mg of plant material was removed from the culture dishes under sterile conditions, and the samples were frozen immediately in liquid nitrogen and stored no longer than 24 hours at −70° C. before being employed in the PCR. 50 μl of the PCR mix stated hereinbelow were placed on the frozen plant material, and the PCR was carried out as shown in the temperature protocol (see hereinbelow). If the plant contains the DNA used for transformation, a 700 bp portion of the npt II gene is amplified with the primer pair PT1/PT2.

Primer PT1: (SEQ ID NO:5) GAGGCTATTCGGCTAT-GACTG

Primer PT2: (SEQ ID NO:6) ATCGGGAGCGGC-GATACCGTA

PCR mix:

41 μl H$_2$O; 5 μl 10×PCR buffer containing MgCl$_2$ (AGS), 0.5 μl dNTP mix (Pharmacia; 200 mM), 1.5 μl primer PT1 (15 pmol); 1.5 μl primer PT2 (15 pmol); 0.5 μl Taq DNA polymerase (2U).

Temperature protocol:
1. 95° C. 1 min
2. 60° C. 1 min
3. 72° C. 2 min
4. 95° C. 45 s
5. 60° C. 1 min
6. 72° C. 2 min (40 cycles steps 4–6)
7. 4° C. until further use 17) PCR with Isolated Genomic DNA:

The PCR described was likewise used for detecting the npt II gene from genomic DNA. 500 ng were employed as template DNA. PCRs with the primer pairs Ppf4/RT1 and RT4/Ppf5 and 500 ng total DNA were carried out to analyze a homologous recombination in the transformation with the gene disruption construct for the ftsZ gene. Again, the reaction mix contains the components stated under item 16) of the description.

Primer Ppf4:(SEQ ID NO:7) GGAGCTGACATG-GTTTTCGT

Primer RT1:(SEQ ID NO:8) TGTCGTGCTCCACCAT-GTTG

Primer RT4:(SEQ ID NO:9) GTTGAGCATATAA-GAAACCC

Primer Ppf5:(SEQ ID NO:10) AACCCATACTTAAC-TAGGCA

The following temperature protocol was used:
1. 95° C. 1 min
2. 55° C. 1 min
3. 72° C. 2 min 30 s
4. 95° C. 45 s
5. 55° C. 1 min
6. 72° C. 2 min 30 s
7. 95° C. 45 s
8. 55° C. 1 min
9. 72° C. 5 min (40 cycles step 7–9)
10. 4° C. until further use 18) DNA Sequencing Sequencing was effected as described by Sanger et al. (1977 Proc. Natl. Acad. Sci. USA 74, 5463–5467) using the ABI PRISM™ Dye Terminator Cycle Sequencing Core Kit (Perkin Elmer, Weiterstadt) and an automatic 373A sequencer from Applied Biosystems (Weiterstadt). Instead of the recommended amount of template and primer, 1.5 mg of template DNA and 15 pmol of primer were employed. To sequence PCR amplificates, the PCR reaction was purified with the Nucleotrap PCR Extraction Kit from Macherey-Nagel (Düren) and sequenced with the primers employed for amplification.

19) Electron Microscopy:

Moss protonemata from liquid culture were fixed for three hours in 2.5% glutaraldehyde/0.05 M phosphate buffer pH 7 at 4° C. (Geyer, G. 1973 in: Ultrahistochemie, Gustav Fischer Verlag Stuttgart). After three washes in phosphate buffer, the samples were incubated overnight at 4° C. in 1% (w/v) osmium tetroxide (OsO$_4$)/0.1 M cadodylate buffer pH 7.2 (Geyer, G. 1973 in: Ultrahistochemie, Gustav Fischer Verlag Stuttgart) and then washed repeatedly with cadodylate buffer, transferred into 1% (w/v) agar and dehydrated in a graded alcohol series (15–100%). The material was then embedded in Spurr medium (Spurr, A. R. 1969, J. Ultrastr. Res. 26, 31–43).

Ultra-thin sections of the samples were prepared with the aid of an IomU2 ultramicrotome (Reichert-Jung, Leica, NuBloch, Germany) and trasferred to copper grids coated with Mowital (Hoechst). The sections were post-contrasted for 15–20 minutes with a saturated uranyl acetate solution in 70% methanol (Schreil, W. 1964, J. Cell Biol. 22, 1–20) and subsequently incubated for 10–15 min with lead citrate (Reynolds, E. S. 1963, Cell Biol. 17, 208–21). Samples were evaluated under the electron microscope operating at 80 kV.

Key to the figures:

FIG. 1: Schematic representation of the vector pFDX3840 suitable for cloning eukaryotic nucleotide sequences and transfer into microorganisms.

FIG. 2: Schematic representation of vector pFDX3840::insert additionally comprising eukaryotic nucleotide sequences suitable for transfer into microorganisms for the purposes of the subsequent transposon mutagenesis.

FIG. 3: Schematic representation of the vector pFDX3840::mutated-insert comprising eukaryotic nucleotide sequences (cDNA insert) genetically modified by transposon integration (mini-Tn1000::nptII), which nucleotide sequences, in turn, are suitable for homologous recombination in eukaryotic cells.

FIG. 4: Schematic representation of the conjugative plasmid pFDX3833 comprising the mini-transposon Tn1000::nptII.

FIG. 5: Schematic representation of the vector pFDX3842, a derivative of the vector pFDX3840, which is likewise suitable for cloning eukaryotic nucleotide sequences and transfer into microorganisms. It differs from vector pFDX3840 by a different polylinker for cloning eukaryotic DNA.

FIG. 6: Schematic representation of vector pFDX3844, a derivative of vector pFDX3840, which is likewise suitable for cloning eukaryotic nucleotide sequences and transfer into microorganisms. It differs from vectors pFDX3840 and pFDX3842 by a smaller selection of recognition sites for single restriction endonucleases (polylinkers) for cloning eukaryotic DNA.

We claim:

1. A method for mutagenesis of eukaryotic nucleotide sequences, which comprises:
   a) transferring a genomic nucleotide sequence or a cDNA sequence from a eukaryotic organism to a microorganism,
   b) genetically modifying the genomic nucleotide sequence or the cDNA sequence in the microorganism by sequence-independent insertion mutagenesis via cointegrate formation during conjugation between two microorganisms, and
   c) isolating the genetically modified, genomic nucleotide sequence or cDNA sequence from the microorganism.

2. A method as claimed in claim 1, wherein the genomic nucleotide sequence or the cDNA sequence originates from plants, algae or fungi.

3. A method as claimed in claim 1, wherein the mutagenesis is effected with high efficiency with a relative frequency post-selection in a range of from approximately 90 to 100%.

4. A method as claimed in claim 1, wherein a vector comprising a nucleotide sequence and additional functional nucleotide sequences is transferred to said microorganism.

5. A method as claimed in claim 1, wherein a population of different eukaryotic nucleotide sequences is generated by sequence-independent mutagenesis based on a selected region of a eukaryotic nucleotide sequence.

6. A method as claimed in claim 1, wherein the mutagenesis is effected by insertion of a heterologous nucleotide sequence.

7. A method as claimed in claim 6, wherein the heterologous nucleotide sequence is a transposon.

8. A method as claimed in claim 1, wherein the microorganism comprises characteristics for transposition and conjugation.

9. A method as claimed in claim 1, wherein the microorganism is a bacterium of the family Enterobacteriaceae or Bacillaceae.

10. A method as claimed in claim 1, wherein the mutagenesis is effected with high efficiency at a relative frequency post-selection in a range of from approximately 90 to 99%.

11. A method as claimed in claim 1, wherein the mutagenesis is effected with high efficiency at a relative frequency post-selection of approximately 99.9%.

12. A method as claimed in claim 4, wherein the vector comprises one or more of the characteristics of pFDX3840::insert.

13. A method as claimed in claim 4, wherein the vector comprises one or more of the characteristics of pFDX3842.

14. A method as claimed in claim 4, wherein the vector comprises one or more of the characteristics of pFDX3844.

15. A method as claimed in claim 6, wherein the heterologous nucleotide sequence is of prokaryotic origin.

16. A method as claimed in claim 7, wherein the transposon comprises mini-Tn1000::nptll.

* * * * *